(12) United States Patent
Hauck et al.

(10) Patent No.: US 8,911,382 B2
(45) Date of Patent: Dec. 16, 2014

(54) CATHETER WITH PULL WIRE MEASUREMENT FEATURE

(75) Inventors: John A. Hauck, Shoreview, MN (US); Mark T. Johnson, Mounds View, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1008 days.

(21) Appl. No.: 12/716,056

(22) Filed: Mar. 2, 2010

(65) Prior Publication Data

US 2011/0218491 A1 Sep. 8, 2011

(51) Int. Cl.
*A61B 5/00* (2006.01)
*A61M 31/00* (2006.01)
*A61M 37/00* (2006.01)
*A61M 25/00* (2006.01)
*A61M 25/098* (2006.01)

(52) U.S. Cl.
USPC ............... 600/585; 604/95.04; 604/95.05; 604/523; 604/528; 604/529

(58) Field of Classification Search
USPC ............ 600/585; 604/95.04, 95.05, 523, 528, 604/529
See application file for complete search history.

(56) References Cited

U.S. PATENT DOCUMENTS

| | | | | |
|---|---|---|---|---|
| 4,570,354 | A * | 2/1986 | Hindes | 33/534 |
| 4,715,128 | A * | 12/1987 | Cummings et al. | 33/544 |
| 5,238,005 | A * | 8/1993 | Imran | 600/585 |
| 6,370,411 | B1 * | 4/2002 | Osadchy et al. | 600/372 |
| 7,972,298 | B2 | 7/2011 | Wallace et al. | |
| 8,256,123 | B2 * | 9/2012 | Lee et al. | 33/1 PT |

* cited by examiner

*Primary Examiner* — Devin Henson
(74) *Attorney, Agent, or Firm* — Dykema Gossett PLLC (57) ABSTRACT

An apparatus for determining a length of a portion of a steering wire disposed within a bendable medical device includes an electrical contact slidably coupled with a steering wire, an electrical source configured to transmit an electrical signal through a portion of the steering wire, and a processor configured to monitor a parameter of the electrical signal at or about the electrical contact and configured to determine a length of a portion of the steering wire using the monitored parameter.

19 Claims, 8 Drawing Sheets

FIG.7

CATHETER WITH PULL WIRE MEASUREMENT FEATURE

BACKGROUND OF THE INVENTION a. Field of the Invention

The present disclosure relates to catheter devices and systems, including devices and methods for determining angle or degree of bend/deflection, as well as the location and orientation of a catheter and/or sheath within a treatment area.

b. Background Art

Electrophysiology (EP) catheters are used in connection with an ever-increasing number of procedures. Such catheters have been used, for example, for diagnostic, therapeutic, mapping, and ablative procedures. Catheters are commonly manipulated through a patient's vasculature to an intended site, for example a site within the patient's heart, and may carry one or more electrodes that may be used for mapping, ablation, diagnosis, or other treatments.

Traditional techniques for manipulating catheters to, and within, a treatment area generally require a user to manipulate a handle connected to a catheter. The handle commonly includes a mechanism connected to steering wires that controls the deflection of the associated catheter. A second handle is often provided for controlling deflection of an associated sheath. Rotating and advancing a catheter or sheath generally requires an electrophysiologist to physically rotate and advance the associated handle. Alternatively, a robotic system may be employed to manipulate the pull wires and control distal deflection. With either method, knowledge of the distal bending characteristics and position of the catheter is commonly utilized.

To determine position and bending characteristics, a feedback system may be used to provide the location of the catheter. Feedback systems typically externally monitor the catheter's position in three dimensional space, and provide information concerning the associated movement of a catheter to a user. Exemplary feedback systems include the EnSite NavX™ impedance-based system commercialized by St. Jude Medical, Inc., as well as the magnetically-based Medical Positioning System (gMPS) for navigation developed by St. Jude Medical, Inc. through its MediGuide Inc. business unit of Haifa, Israel. Some feedback systems may, however, simply be reactionary, in that they may simply determine the direction and magnitude of a movement after the movement has been made.

The three-dimensional location and distal bending characteristics of a catheter may be predicted if the displacement status of the steering wires is known. In particular, deflection characteristics are affected by the length of steering wires extending beyond a fulcrum (i.e., the location or point at which deflection begins). By knowing the respective distal steering wire lengths, along with the current catheter position, a new position can be expressed in terms of a steering wire movement. Conventional prediction methods generally monitor steering-wire length at the proximal end of the catheter with the assumption that the proximal steering wire movement is directly related to the distal steering wire movement. In practice, however, the steering wires extending to the distal end of the catheter may be a meter or more in length, and may be affected by a number of factors, including compression in the catheter body, stretching of pull wires, curvature of the proximal body of the catheter, and other anomalies. Current prediction methods thus may not always provide accurate prediction of distal steering wire lengths.

BRIEF SUMMARY OF THE INVENTION

An apparatus for determining a length of a portion of a steering wire disposed within a bendable medical device includes an electrical contact slidably coupled with a steering wire, an electrical source configured to transmit an electrical signal through a portion of the steering wire, and a processor configured to monitor a parameter of the electrical signal at or about the electrical contact and configured to determine a length of a portion of the steering wire using the monitored parameter. The apparatus may further include a second electrical contact slidably coupled with a second steering wire, an electrical source configured to transmit an electrical signal through a portion of the second steering wire, and a processor configured to monitor a parameter of the electrical signal at or about the second electrical contact and configured to determine a length of a portion of the second steering wire using the monitored parameter. The processor may be configured to determine a heading angle, a deflection angle, or a Cartesian movement of a portion of the bendable medical device from a determined length of a portion of one or more steering wires.

DETAILED DESCRIPTION OF THE INVENTION

Figure 1:
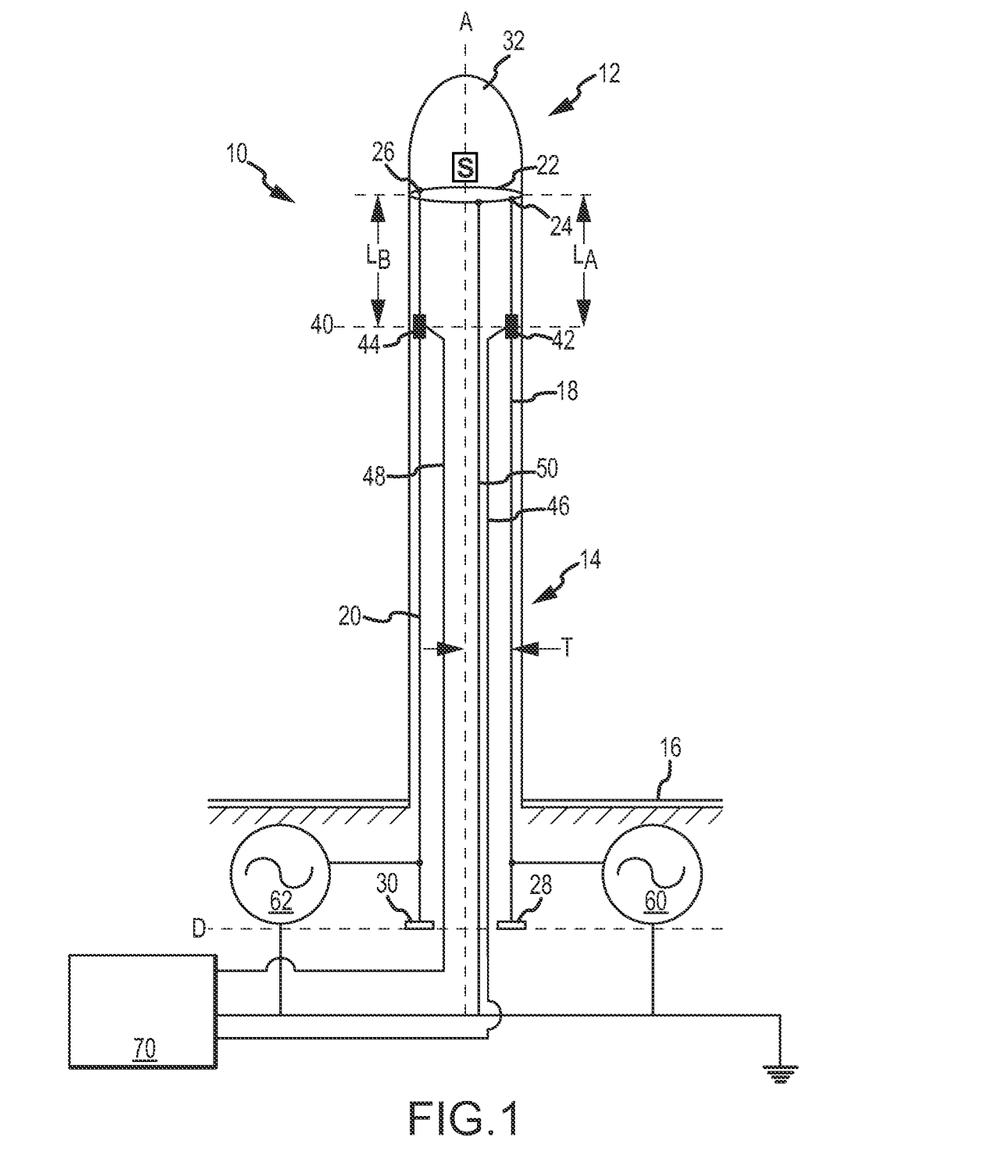
FIG. 1 is a general representation of a catheter according to an embodiment of the invention, the catheter shown in an undeflected state.

Referring to the drawings, wherein like reference numerals are used to identify like or identical components in the various views, FIG. 1 generally illustrates a catheter 10 that is provided in an undeflected state along longitudinal axis A. As illustrated, catheter 10 includes a distal portion 12 and a proximal portion 14. The proximal portion 14 of catheter 10 may be rigidly connected or attached to a support base 16. Support base 16 may, for example, comprise a conventional catheter handle, or a portion of a cartridge (e.g., a disposable cartridge) that may be configured to interface with a robotic catheter manipulation system or assembly.

Catheter 10 may include a position sensor S, operatively coupled to a portion of the device, that is configured to provide an indication of the position and/or orientation of a portion of the catheter 10. Position sensor S may be a non-contact position sensor that may sense a provided electrical or magnetic field. In an embodiment, position sensor S may comprise one or more electrodes, such as electrode rings, that are configured to be used in an impedance-based positioning system, such as the EnSite NavX™ impedance-based system commercialized by St. Jude Medical, Inc. In an embodiment, position sensor S may comprise one or more sensor coils configured to generate a signal in response to a magnetic field, such as with the magnetically-based Medical Positioning System (gMPS) for navigation developed by St. Jude Medical, Inc. through its MediGuide Inc. business unit of Haifa, Israel.

As generally illustrated, catheter 10 may include at least two steering wires 18, 20, each longitudinally situated within and along a substantial length of the catheter 10. It is understood that while two steering wires are illustrated, the disclosure is not so limited, and more than two steering wires may be provided. In embodiments, the steering wires may be comprised of a material having known resistance/impedance properties or qualities. For example and without limitation, in an embodiment, steering wires 18, 20 may be comprised of 32 AWG stainless steel, which is known to have a resistance of approximately 40 milliohms per millimeter. Catheter 10 may further include one or more electrical contacts 42, 44 that may be positioned along the length of the catheter and may be in electrical communication with steering wires 18, 20. For example, as generally shown in the illustrated embodiment, such electrical contacts 42, 44 may comprise one or more ferrules that may be located in or near the distal portion 12 of catheter 10, and which may be positioned at or about a fulcrum 40. The electrical contacts 42, 44 may alternatively comprise, for example and without limitation, electrical contact brushes, slip rings, or other coupling elements presently known or hereafter developed.

The one or more electrical contacts 42, 44 may be configured to maintain slidable contact with steering wires 18, 20 and are generally configured to not significantly impede the translation of the respective steering wire, in an embodiment, electrical contacts 42, 44 may have a generally annular shape and an inner diameter sized to conform closely to the outer diameter of the steering wires 18, 20. Catheter 10 may further include a pull ring 22, which may take the form of a rigid ring firmly connected or affixed to a portion of catheter 10 at a position that is more distal than the fulcrum 40. The distal portion of each steering wire 18, 20 may be connected to pull ring 22 via a rigid connection or coupling, and may connect to the pull ring 22 at given points 24, 26. In an embodiment, such a rigid connection or coupling may include a weld, braze, or other known means of attachment.

As generally depicted in the illustrated embodiment, proximal portions of steering wires 18, 20 may be respectively connected to control members 28, 30. Control members 28, 30 may be used, for example, to interface with and/or operatively connect to and control the movement of portions of the device via steering wires 18, 20. In embodiments, the control members 28, 30 may interface with or be operatively connected to respective actuators of a robotic catheter manipulator. In other embodiments, the control members 28, 30 may be interfaced with or operatively connected to manually controlled actuators, such as provided in some conventional catheter handles. For illustrative purposes, as generally shown in FIG. 1, when catheter 10 is configured in an undeflected state on longitudinal axis A, control members 28, 30 may both be situated at or about one or more initial or common reference levels or datum (e.g., common datum D shown in FIG. 1). However, for some embodiments, no initial relationship of control members 28, 30 is necessary, and the positioning of each control member may, for instance, be unspecific (e.g., it may be a consequence of initial assembly). Further, as is generally illustrated, when in an undeflected state, the distance between fulcrum 40 and the pull ring 22 of steering wires 18 and 20, denoted by $L_A$ and $L_B$, respectively, may be approximately equal.

In an embodiment, catheter 10 further includes a tip 32 that may be used to perform various medical treatments or procedures. Tip 32 may include one or more electrodes, therapy delivery devices, ultrasound sensors, and/or location determining elements. In an embodiment, for example, catheter tip 32 may include one or more mapping electrodes that are configured to detect physical or electrical characteristics of cardiac tissue. In embodiments, tip 32 may, instead or additionally, include one or more ablation electrodes configured to, for example, create lesions within cardiac tissue during an ablation procedure. It is noted, however, that the disclosure is not limited to a particular type or form of catheter tip. Embodiments of the disclosed concept may further include tips including various combinations of catheter tip features.

Catheter 10 may be coupled with one or more electrical sources (e.g., electrical sources 60, 62) that are configured to transmit an electrical signal through at least a portion of one or more steering wires. In an embodiment, one or more electrical sources 60, 62 may be coupled to steering wires 18, 20 through a connection (e.g., a direct connection) with a portion of the proximal end of each respective steering wire. Alternatively, the electrical sources 60, 62 may be electrically coupled to steering wires 18, 20 via one or more ferrules, brushes, slip rings, or other similar coupling elements or methodologies. In an embodiment, the one or more electrical sources may be coupled to steering wires 18, 20 at a location located within the body of the catheter.

Each of the one or more electrical sources (e.g., electrical sources 60, 62) may be configured as either a voltage source or a current source, and may be further configured to provide a signal along at least a portion of the respective steering wires 18, 20. As used herein, a current source may be, for example and without limitation, a resistor current source that includes a voltage source in series with a resistor. In another embodiment, a current source may be a more complex circuit that may include, for example, an amplifier with feedback derived from a sense resistor. In an embodiment, each electrical source is a current source that is configured to output an RMS current signal in the range of 0-10 mA, and for some embodiments may output a signal in the range of 10-1000 uA. It is understood that the selection of the signal output strength may be largely dependent on the noise floor of the system and can be adjusted upward for noisier systems. In an embodiment, each electrical source may be configured to provide an AC signal at one or more particular transmission frequencies. Alternatively, each source may be configured to provide a DC signal.

As generally depicted in the illustrated embodiment in FIG. 1, catheter 10 may further include two electrical contact wires 46, 48, such as ferrule wires, that are electrically coupled to respective electrical contacts 42, 44. Similarly, catheter 10 may have at least one pull ring wire 50 coupled to pull ring 22. Each electrical contact wire 46, 48 and pull ring wire 50 may be further coupled or operatively connected to a processor 70. Processor 70 may be, for example, a single integrated processor, or a collection of discrete components, and may be configured to receive electrical signals from each electrical contact wire 46, 48 and pull ring wire 50. Processor 70 may additionally be coupled or operatively connected to electrical sources 60, 62 and configured to vary at least one parameter of source output. By way of example, without limitation, such parameters may include the frequency and/or magnitude of the output signal. In an embodiment, processor 70 may include high impedance amplifiers configured to receive a signal from one or more of the steering wires 18, 20, the electrical contact wires 46, 48, or the pull ring wire 50. Processor 70 may be comprised of hardware, or may include a combination of hardware and software.

Figure 2:
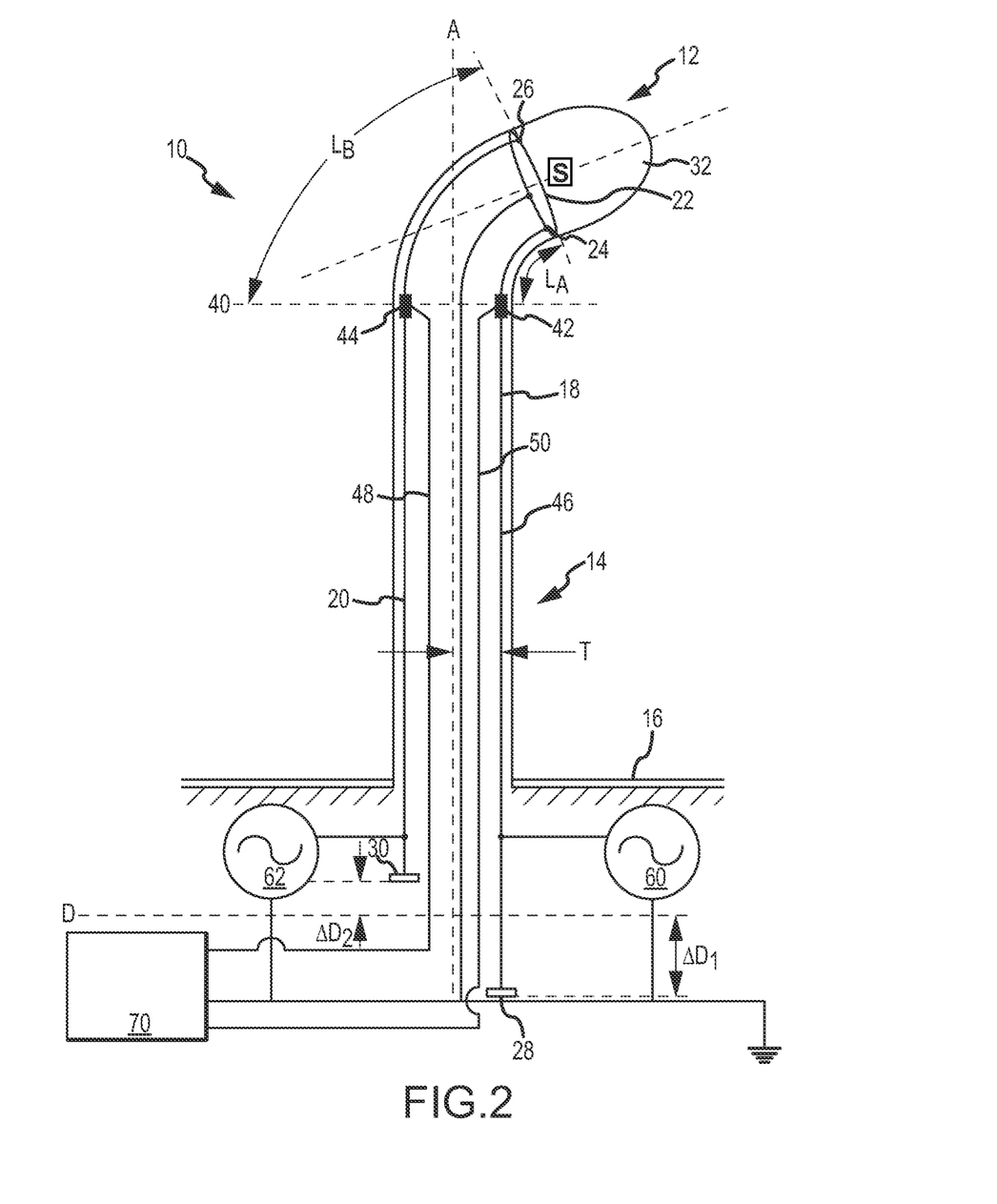
FIG. 2 is a general representation of a catheter of the type illustrated in FIG. 1, the catheter shown in a deflected state.

As generally illustrated in FIG. 2, the distal portion 12 of catheter 10 may be deflected or displaced from longitudinal axis A by selective actuation or tensioning of one or more steering wires. For example, control member 28 may be translated in a proximal direction a distance $\Delta D_1$, which causes a tensioning of, or tension response in, steering wire 18. The actuation of steering wire 18 will cause a corresponding deflection of the distal portion 12 of catheter 10 in a direction toward steering wire 18. As illustrated generally in FIG. 2, deflection of the distal portion 12 of the catheter 10 generally begins at or about the fulcrum 40. In the illustrated embodiment, the fulcrum 40 may define the line or point(s) along the length of the catheter at which the catheter 10 transitions from a relatively stiffer or firmer proximal portion, to a relatively more bendable distal portion. In an embodiment, such increased bendability may be associated with the use of a material having a lesser durometer in the distal portion than in the proximal portion of the catheter. Alternatively, the fulcrum 40 may define a transition point or portion of the catheter where the structure, such as the internal structure of the catheter, is modified in a manner (including methodologies known in the art) to promote distal bending.

Figure 3A:
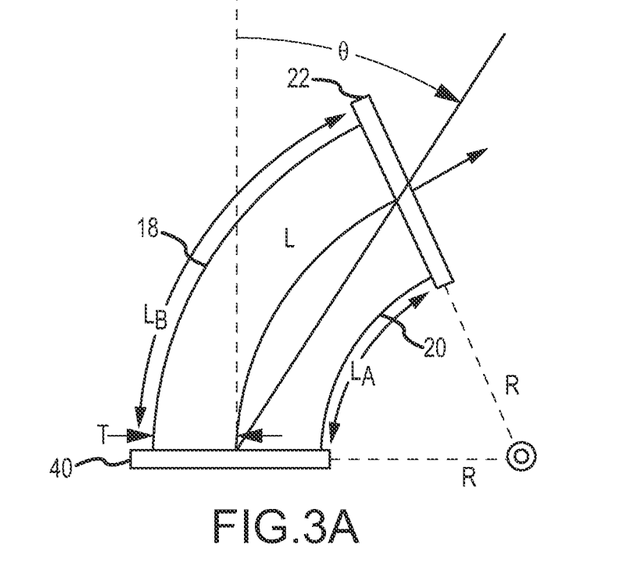
FIG. 3A is a schematic representation of a bendable portion of a catheter illustrating a deflection angle.
Figure 3B:
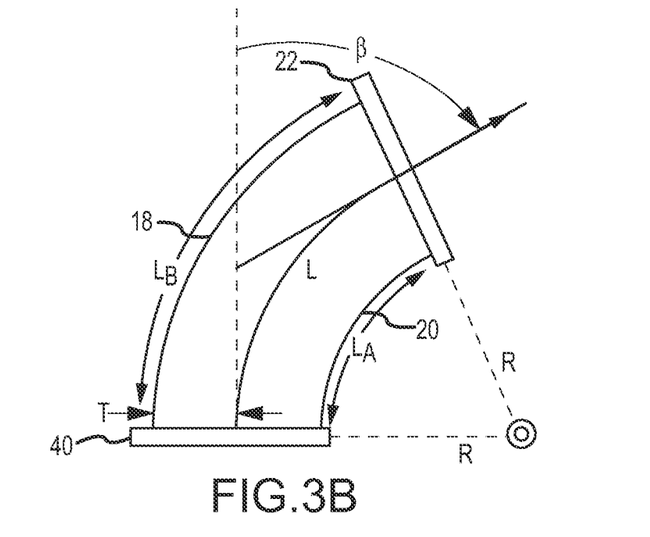
FIG. 3B is a schematic representation of a bendable portion of a catheter illustrating a heading angle.

As illustrated in FIG. 2, and more generally in FIGS. 3A and 3B, actuation of steering wire 18 in a proximal direction may cause a reduction in the length of steering wire 18 beyond fulcrum 40 (i.e., length $L_A$). Further, while control member 28 is actively translated a distance $\Delta D_1$ in a first proximal direction, control member 30 may reactively move or retract a distance $\Delta D_2$ in a second, substantially opposing distal direction, which may be associated with a corresponding increase in the length of steering wire 20 beyond fulcrum 40 (i.e., length $L_B$). The reactive motion of control member 30 and steering wire 20 may depend on the difference in arc lengths between the two steering wires. Assuming the distal portion bends with a constant radius of curvature, the arc lengths of the steering wires would then be a function of a transverse distance—e.g., distance T between steering wire 18 and the central longitudinal axis A—and the bending radius of curvature R of the distal portion 12.

As generally illustrated in FIGS. 3A and 3B, in a two-steering wire configuration, where a constant curvature is assumed, the planar deflection of catheter 10 can generally be expressed as a function of the nominal length of the catheter between fulcrum 40 and pull ring 22 (i.e., length L), and either a heading angle β or a deflection angle θ. Assuming the relevant portion of the catheter has a substantially uniform thickness (i.e., 2T) and lengths $L_A$ and $L_B$ of the steering wires are known, the nominal length L can be determined using equation (1), and deflection angle θ can be determined using equation (2). Furthermore, in a planar configuration, the heading angle β will generally be twice the deflection angle θ.

$$L = \frac{L_A + L_B}{2} \tag{1}$$

$$\theta = \frac{L_B - L_A}{2} \times \frac{1}{2T} \tag{2}$$

The Cartesian deflection of the catheter within the deflection plane can further be approximated or estimated using equation (3), where (x, y) are Cartesian coordinates within the plane.

$$(x, y) = \left( \frac{L\sin(\theta)}{\theta} \sin(\theta), \frac{L\sin(\theta)}{\theta} \cos(\theta) \right) \tag{3}$$

Referring again to FIGS. 1 and 2, displacements $\Delta D_1$ and $\Delta D_2$ will theoretically bear a linear relationship to each other, and should also mirror the motion of $L_A$ and $L_B$, respectively. In practice, however, tensile strain of the steering wires and non-uniform axial compression of the catheter 10 may cause the relationship between $\Delta D_1$ and $\Delta D_2$ to be non-linear. Additionally, if the catheter, as shown in FIG. 2, is retracted back to an undeflected state along longitudinal axis A (i.e., θ=0; $L_A=L_B$), control members 28, 30 would ideally be returned to their original positions. In practice, however, memory effects of the catheter 10 may cause the control members 28, 30 to return to a different position. Therefore, obtaining measurements of wire length at the proximal end of steering wires 18, 20 may not always completely or accurately indicate position of the distal end 12 of catheter 10.

To help address/avoid certain catheter non-linearities and wire stretch, it can be desirable to determine the deflection of the distal portion of the catheter directly from the lengths of the steering wires between the fulcrum 40 and the pull ring 22 (i.e., lengths $L_A$, $L_B$). In one approach, these lengths may be determined by measuring the electrical characteristics of the steering wires. In an embodiment, an electrical current may be passed through each steering wire 18, 20, and the voltage drop between the fulcrum 40 and the pull ring 22 (which may comprise the bendable portion) may be monitored. Knowledge of the transmitted current and the inherent resistance of the steering wire may then be used to convert the associated voltage drop to a length. This process is conceptually illustrated in FIG. 4. As shown, in the exemplary embodiment of FIG. 4, a known current may be generated by a source 160. A sensor 170, may be connected to steering wire 120 through an electrical contact 140 (e.g., a slidable electrical contact) positioned at the fulcrum 40. Pull ring 22 may be connected to ground. The sensor 170 may be configured to monitor the voltage at the electrical contact 140, which corresponds to the voltage drop across the bendable portion 150 (which corresponds to the segment provided between the fulcrum 40 and pull ring 22). The resistance $R_2$ of steering wire 120 should equal the voltage sensed by sensor 170, divided by the current generated by source 160. This computed resistance can then be used, together with the known resistance per unit length of the steering wire, to compute the length of the steering wire present within the bendable portion 150.

Figure 5:
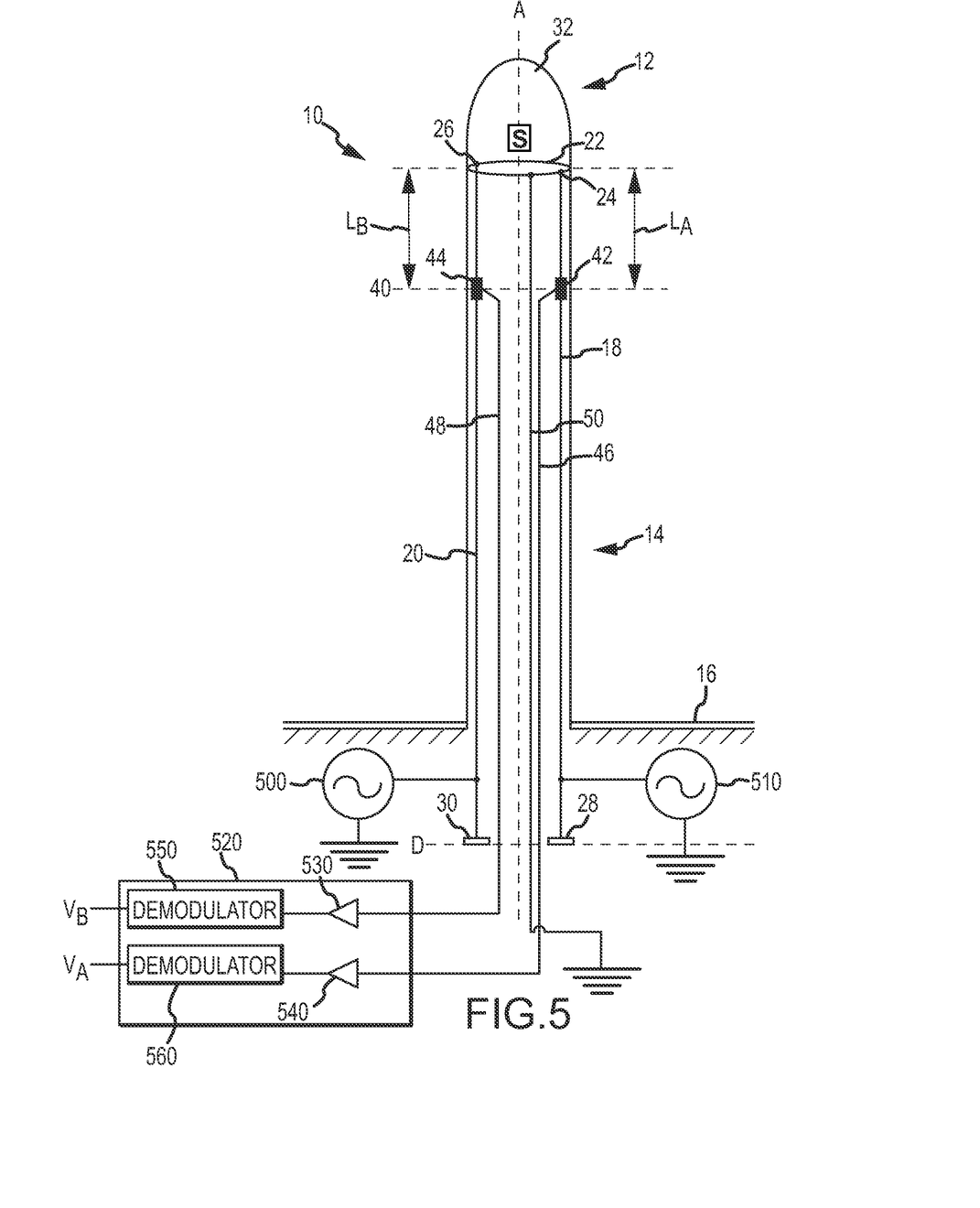
FIG. 5 is a representation of a catheter pull wire measurement device according to an embodiment of the disclosure.

FIG. 5 generally illustrates an embodiment of catheter 10 that is configured to determine the length of steering wires 18, 20 extending from electrical contacts 42, 44 to pull ring 22. In the illustrated embodiment, current sources 500, 510 are coupled to steering wires 20, 18, respectively, and are configured to drive electrical current therethrough. In the illustrated embodiment, pull ring wire 50 may serve as a return wire to complete a circuit with respect to current sources 500, 510, or may instead be connected as a relative ground (such as generally depicted in FIG. 5). Current sources 500, 510, may be configured to provide AC currents at different frequencies to different respective steering wires 18, 20. A processor 520 may be configured to receive electrical signals from, for example, electrical contact wires 46, 48. An embodiment of the processor 520 may include a first amplifier 530 and a second amplifier 540. In an embodiment, amplifiers 530, 540 may be high impedance amplifiers that are configured so as not to significantly affect the current driven through the steering wires 18, 20. Amplifier 530 may be configured as a standard inverting amplifier and may receive an input from electrical contact wire 48. Due to its high impedance characteristics, amplifier 530 may draw a negligible current, and thus, the input from electrical contact wire 48 may represent the voltage at electrical contact 44. Similarly, amplifier 540 may receive an input from electrical contact wire 46, which represents the voltage at electrical contact 42. Each amplifier 530, 540 may receive an electrical signal from a pull ring wire 50 as a second input, which may be considered a system reference or ground. The output of each amplifier 530, 540, may be provided to a respective demodulator 550, 560, where the received signal may be demodulated at the frequency of the current source 500, 510 that drives each respective steering wire 18, 20. The voltages $V_A$, $V_B$ that are recovered from the electronic circuit may then be linearly related to the resistance of the respective steering wires 18, 20, between the electrical contacts 42, 44, and the system reference. Note that the resistance of the return wire 50 between the pull ring 22 and the system reference is a constant value, whereas the resistance contribution of the steering wires extending from the electrical contacts 42, 44 will change as lengths $L_A$, $L_B$ change. The resistances change in a proportional, linear manner with the change of lengths $L_A$, $L_B$. For example, 32 AWG stainless steel has a resistance of approximately 40 milliohms per millimeter, so a change of 0.1 millimeters would result in a change of 4 milliohms RMS. It is contemplated that 3-4 milliohms is within the signal to noise ratio capability of the disclosed embodiments. Accordingly, the system may be configured to support dynamic, real-time measurement of steering wire lengths, with sub-millimeter accuracy.

Figure 6A:
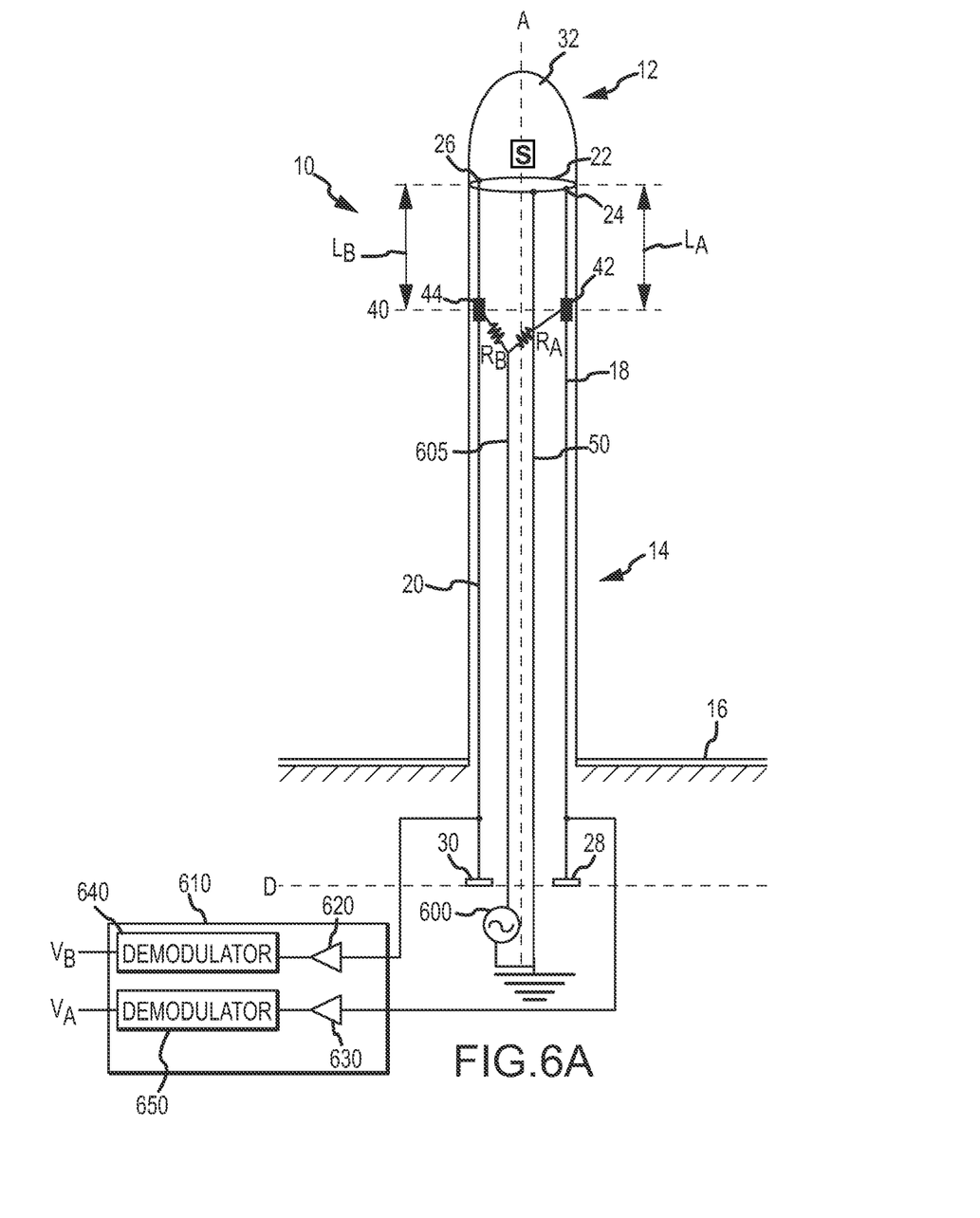
FIG. 6A is a representation of a catheter pull wire measurement device according to an embodiment of the disclosure.

FIG. 6A illustrates another embodiment of a catheter 10 configured to determine the length of steering wires 18, 20 extending from electrical contacts 42, 44 to pull ring 22. In the illustrated embodiment, a voltage source 600 is coupled to each steering wire 18, 20 through an electrical contact wire 605 and respective resistors $R_A$, $R_B$, which creates a current source for each steering wire 18, 20. Resistors $R_A$, $R_B$ may be sized such that the resistance in the remainder of the system is negligible in comparison to their values, and therefore, the current flow through the system is substantially dictated by the resistors $R_A$, $R_B$. For example, without limitation, $R_A$ and $R_B$ may be 10 KΩ resistors. In an embodiment, voltage source 600 may provide an AC signal. A pull ring wire 50 may be coupled to the pull ring 22, and the pull ring wire 50 may be configured to serve as a return conductor and/or relative ground for voltage source 600. High impedance amplifiers 620, 630 may be coupled with proximal ends of respective steering wires 20, 18, and can be configured to receive the voltage level at electrical contacts 44, 42 without substantially affecting current flow. Outputs of the amplifiers 620, 630 may be coupled to respective demodulators 640, 650 to determine the respective magnitudes of the voltage drop across lengths $L_A$, $L_B$, of steering wires 20, 18 extending from electrical contacts 42, 44.

Figure 6B:
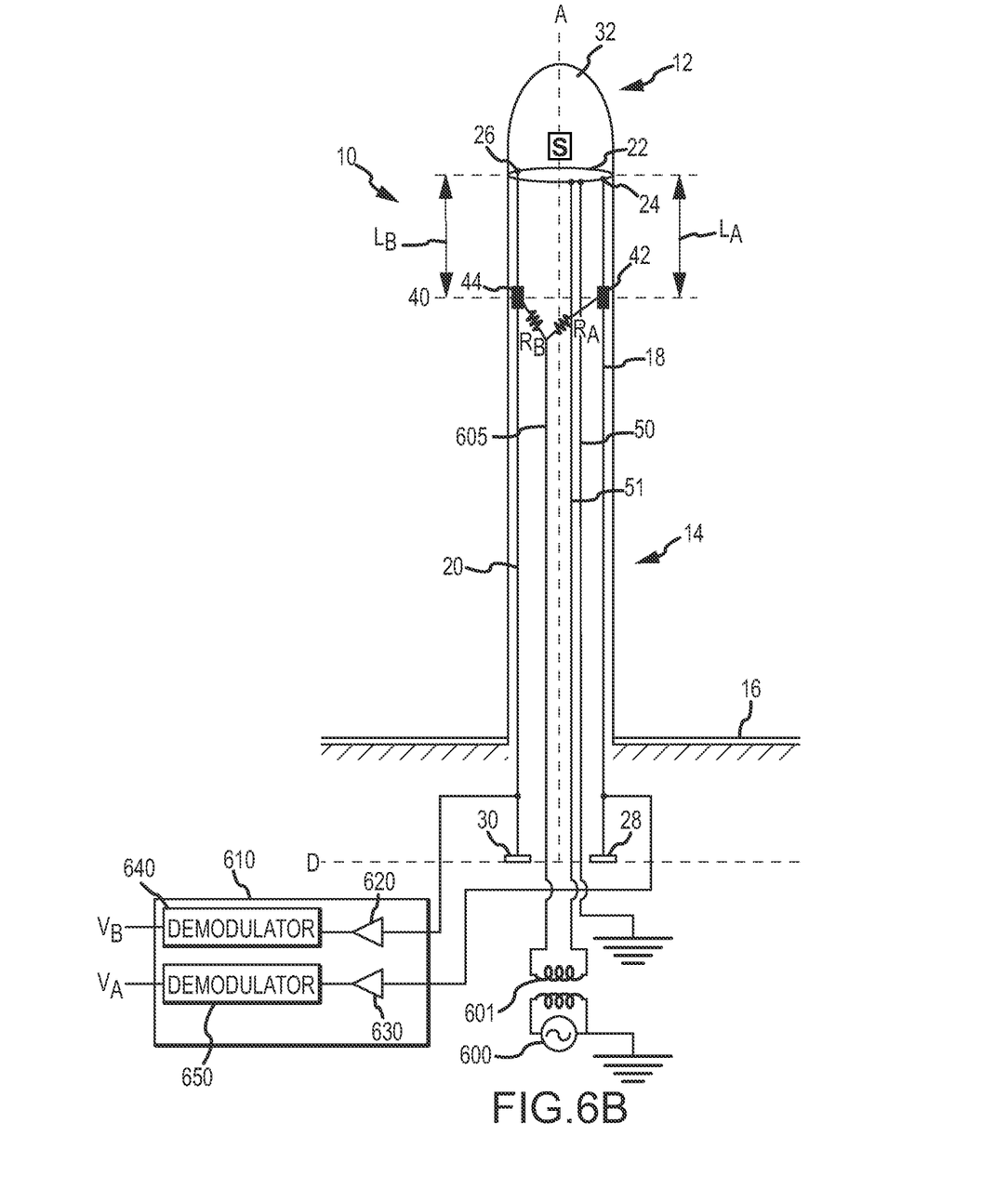
FIG. 6B is a representation of a catheter pull wire measurement device according to an embodiment of the disclosure.

FIG. 6B illustrates another embodiment of catheter 10 configured to determine the length of steering wires 18, 20 extending from electrical contacts 42, 44 to pull ring 22. In the illustrated embodiment, voltage source 600 is isolated from the remainder of the catheter through the use of, for example, an isolation transformer 601. A return wire 51 is configured to provide a return path for the isolated loop. The catheter may further be configured with a pull ring wire 50, which may establish a local voltage reference or ground reference on pull ring 22.

Figure 4:
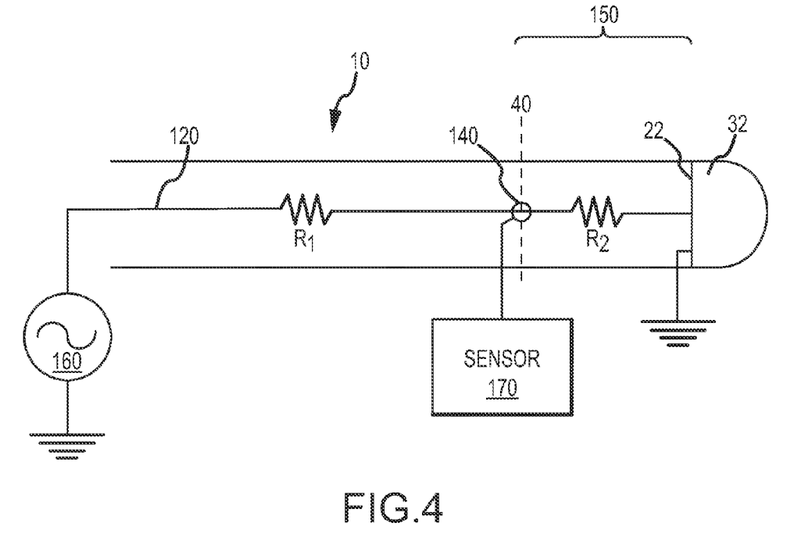
FIG. 4 is conceptual illustration of an embodiment of a catheter pull wire measurement device.

It is understood that, as opposed to the conceptual illustration shown in FIG. 4, the embodiments described with respect to FIGS. 5 and 6A have resistance associated with the pull ring wire that is used to provide a return path for the source. Such resistance may be characterized by the system as part of lengths $L_A$ and $L_B$, though such additional resistance may be measured and accounted for using a common offset. Additionally, in an embodiment, this additional resistance may not specifically be accounted for, though may drop out in computations that are based on the difference in pull wire lengths $L_A$ and $L_B$. In the embodiment illustrated in 6B, the use of an isolated source 600, dedicated current return wire 51, and a separate pull ring ground reference may provide for a measurement of $L_A$ and $L_B$ that is independent of an offset caused by the pull ring wire resistance.

Figure 7:
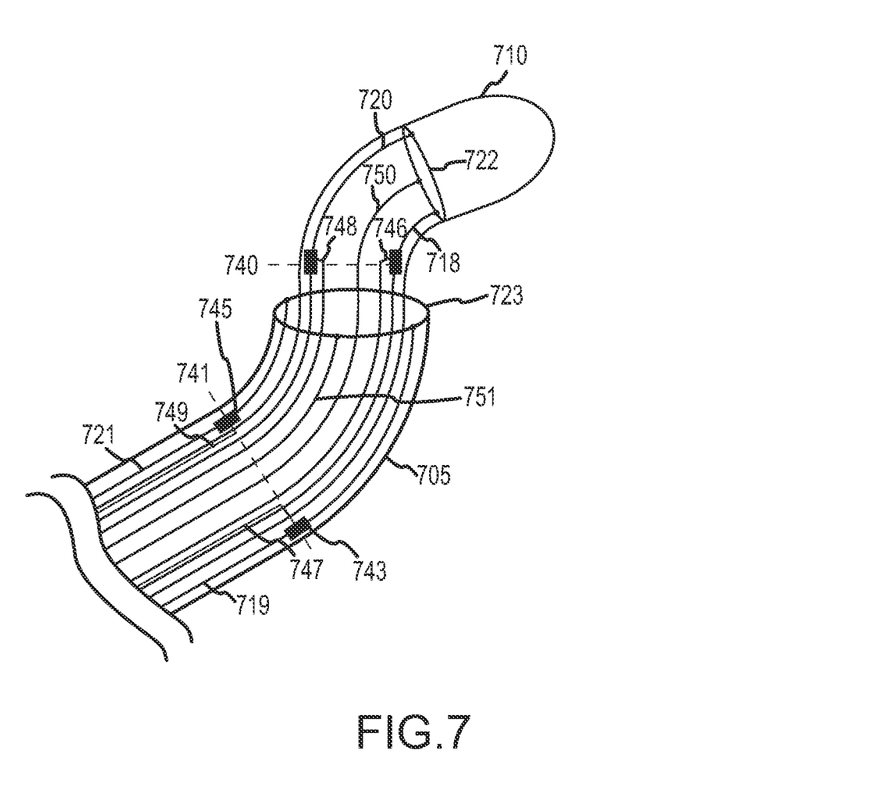
FIG. 7 is a representation of a catheter and a sheath according to an embodiment of the disclosure.

FIG. 7 generally illustrates a medical system including a sheath 705 and a catheter 710 (shown extending beyond the sheath). Generally, existing methods of proximal steering wire length measurement are challenged by the presence of compound curves. With such a curve, as shown in FIG. 7, a sheath 705 may be deflected in one direction, while an associated catheter 710 may be deflected in a substantially different direction. The deflection of sheath 705, and the influence that it has on the catheter steering wires, may make it difficult to determine the deflection characteristics of the associated catheter 710. The present disclosure facilitates determination of such deflection characteristics, because distances can be measured at the distal portion of catheter steering wires 718, 720.

As generally illustrated in FIG. 7, sheath 705 may include sheath steering wires 719, 721 that extend along the length of the sheath. The sheath steering wires 719, 721 may extend through sheath electrical contacts 743, 745 located at or about a sheath fulcrum 741, and may be coupled with a sheath pull ring 723 located distal to the sheath fulcrum 741. Sheath steering wires 719, 721 may further be in electrical contact with sheath electrical contacts 743, 745. Using methods similar to those disclosed above with respect to catheter 10, the lengths of sheath steering wires 719, 721 between the sheath fulcrum 741 and the sheath pull ring 723 may be determined. As further illustrated in FIG. 7, catheter 710 may be advanced within sheath 705 so that the catheter fulcrum point 740 extends from the distal end of the sheath 705 as shown. Moreover, independently from the determination of the sheath steering wire lengths, the system may be configured to determine the lengths of catheter steering wires 718, 720 that extend between catheter fulcrum point 740 and catheter pull ring 722.

Further, catheters and catheter systems such as those described above may utilize or be provided with calibration data. For example, calibration of the system may be provided by placing the device in an "undeflected" position, and determining the nominal zero-point values for the catheter. Zero point values may be stored as voltage readings, current values, lengths, resistance values, and/or any other form of useful information or data. System calibration may also include determining values with the catheter deflected to known angles. Values may be stored for each steering wire, and at varying degrees of deflection. Values may be stored in a manner that is retrievable in connection with the setup or initializations of the system. For example, calibration values may be stored on a memory, such as an EEPROM that may be attached to, or provided with, the catheter. Calibration data may also be stored in a bar code that is readable by a medical system. Additionally, or alternatively, calibration data may be stored on a remote memory that is accessible during setup or initialization of the catheter system. Calibration data may be used, for example, by processors such as processor 70, to provide more accurate data regarding the position of the tip of a respective catheter.

The catheter may likewise be provided with an empirical model of the distal catheter movement that directly relates measured parameters, such as for example, voltage readings, current values, lengths, or resistance values, to a three-dimensional position of the catheter tip. The empirical model may be in the form of a look up table, or a model that employs, for example, regression analysis, neural network modeling, or other empirical techniques. The movement relationships may be determined prior to the actual procedure by experimentally manipulating the catheter throughout its full range of motion, or a portion of the full range of motion, and recording the measured parameters that relate to each of a plurality of poses. In an embodiment, the parameter/position data pairs may be directly populated into a lookup table. In another embodiment, the data pairs may be used to refine a pre-established function, such as in a regression analysis or neural network. While the relationships may be determined from the actual catheter to be used in the procedure, they may alternatively be determined from a catheter that is substantially similar in design or construction to the catheter that will be used. Once the relationships are determined, they may be stored along with the catheter in a manner that is retrievable in connection with the setup, initialization, or use of the system. For example, the model parameters or a lookup table may be stored on a memory, such as an EEPROM, that may be attached to, or provided with, the catheter.

While the foregoing embodiments have generally described catheters including two steering wires, it is to be understood that this is by way of example only, and the devices and methods described herein are also useful for catheters and catheter systems that incorporate three or more steering wires. Moreover, while the foregoing embodiments have been described in relation to a catheter, it is to be understood that this is by way of example and not of limitation, and that those skilled in the art will recognize the applicability of the system to other areas, including sheaths or other bendable medical implements. Additionally, while foregoing implementations have illustrated applications including a single pull ring wire, it is to be understood that this is by way of example and not of limitation. For example, it is contemplated that a catheter may include multiple deflection zones that each have distinct fulcrums and/or pull rings.

Furthermore, while numerous embodiments of this disclosure have been described above with a certain degree of particularity, those skilled in the art could make numerous alterations to the disclosed embodiments without departing from the spirit or scope of the invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed:

1. An apparatus for determining a length of a distal portion of a steering wire disposed within a bendable medical device, the apparatus comprising:
   an electrical contact slidably coupled with the steering wire, wherein the steering wire comprises a proximal end connected to a control member adapted to manipulate the steering wire and control deflection of the bendable medical device;
   a pull ring coupled to a distal portion of the steering wire;
   an electrical source configured to transmit a first electrical signal through the distal portion of the steering wire; and
   a processor configured to monitor a first parameter of the first electrical signal at or about the electrical contact and configured to determine the length of the distal portion of the steering wire using the monitored first parameter;
   wherein the length of the distal portion of the steering wire corresponds to a length of the steering wire between the electrical contact and the pull ring.

2. The apparatus of claim 1, wherein the first parameter of the electrical signal includes a voltage.

3. The apparatus of claim 1, wherein the first parameter of the electrical signal includes a resistance.

4. The apparatus of claim 1, wherein the processor includes an amplifier.

5. The apparatus of claim 1, wherein the electrical source includes an alternating current (AC) source.

6. The apparatus of claim 5, wherein the processor includes a demodulator.

7. The apparatus of claim 1, wherein the electrical source includes a direct current (DC) source.

8. The apparatus of claim 1, wherein the bendable medical device comprises a body, and wherein the electrical source is coupled with the steering wire at a point within the body of the bendable medical device.

9. The apparatus of claim 1, wherein the electrical contact includes a ferrule or brush.

10. The apparatus of claim 1, wherein the electrical source is isolated from the bendable medical device.

11. The apparatus of claim 1, further comprising:
    a pull ring wire coupled to the pull ring and disposed within a length of the bendable medical device.

12. The apparatus of claim 11, wherein the processor is configured to determine the length of the distal portion of the steering wire by at least determining a change in the length of the steering wire between the electrical contact and the pull ring.

13. The apparatus of claim 1, further comprising:
    a second electrical contact slidably coupled with a second steering wire,
    wherein the electrical source is configured to transmit a second electrical signal through a distal portion of the second steering wire, and the processor is configured to monitor a second parameter of the second electrical signal at or about the second electrical contact and is configured to determine a length of the distal portion of the second steering wire using the monitored second parameter.

14. The apparatus of claim 13, wherein the processor is configured to determine a heading angle, a deflection angle, or a Cartesian movement of a portion of the bendable medical device from at least one of the determined length of the distal portion of the first steering wire and the determined length of the distal portion of the second steering wire.

15. The apparatus of claim 13, wherein each of the first electrical signal and second electrical signal has a different frequency.

16. The apparatus of claim 1, wherein the electrical contact is provided proximate a fulcrum of the bendable medical device.

17. The apparatus of claim 1, including an electrically accessible memory configured to store material properties, calibration data, or an empirical model.

18. The apparatus of claim 1, wherein the processor is further configured to correlate the determined of the distal portion of the steering wire to a degree of deflection of the bendable medical device.

19. The apparatus of claim 1, wherein the determined length corresponds to a non-linear segment.

* * * * *